United States Patent
Clerc et al.

(10) Patent No.: US 6,454,720 B1
(45) Date of Patent: Sep. 24, 2002

(54) SYSTEM FOR MEASURING PHYSICAL PARAMETERS WITH A MEDICAL PROBE

(75) Inventors: Jean-Frédéric Clerc, Le Fontanil (FR); François Perruchot, Issy-les-Moulineaux (FR); Stéphane Renard, Champ sur Drac (FR)

(73) Assignees: Commissariat a l'Energie Atomique, Paris (FR); Absys, Clamart (FR)

( * ) Notice: Subject to any disclaimer, the term of this patent is extended or adjusted under 35 U.S.C. 154(b) by 0 days.

(21) Appl. No.: 09/674,833

(22) PCT Filed: May 17, 1999

(86) PCT No.: PCT/FR99/01168

§ 371 (c)(1),
(2), (4) Date: Dec. 15, 2000

(87) PCT Pub. No.: WO99/59467

PCT Pub. Date: Nov. 25, 1999

(30) Foreign Application Priority Data

May 18, 1998 (FR) .............................................. 98 06235

(51) Int. Cl.⁷ ................................................. A61B 5/00
(52) U.S. Cl. ....................... 600/485; 600/549; 600/561; 600/481; 600/505
(58) Field of Search ................................ 600/485, 549, 600/561, 481, 482, 483, 484, 504, 505, 550, 486

(56) References Cited

U.S. PATENT DOCUMENTS

| | | | | |
|---|---|---|---|---|
| 6,053,873 A | * | 4/2000 | Govari et al. ............... | 600/505 |
| 6,248,080 B1 | * | 6/2001 | Miesel et al. ............... | 600/561 |
| 6,264,611 B1 | * | 7/2001 | Ishikawa et al. ............. | 600/486 |
| 6,309,350 B1 | * | 10/2001 | Van Tassel et al. .......... | 600/485 |
| 6,319,208 B1 | * | 11/2001 | Abita et al. .................. | 600/561 |
| 6,336,900 B1 | * | 1/2002 | Alleckson et al. ........... | 600/485 |
| 6,368,275 B1 | * | 4/2002 | Sliwa et al. ................. | 600/549 |
| 6,371,927 B1 | * | 4/2002 | Brune et al. ................. | 600/549 |
| 6,375,624 B1 | * | 4/2002 | Uber, III et al. ............. | 600/549 |
| 6,379,308 B1 | * | 4/2002 | Brockway et al. ........... | 600/486 |

* cited by examiner

Primary Examiner—Teresa Walberg
Assistant Examiner—Fadi H. Dahbour
(74) Attorney, Agent, or Firm—Thelen Reid Priest LLP; Robert E. Krebs

(57) ABSTRACT

The present invention relates to a system for measuring at least one physical parameter in a place in a patient's body to which a medical probe has access, comprising a medical probe (1) equipped with a sensor of said parameter and means for emitting an electrical signal that represents said parameter and that is received by the sensor, to a data processing device outside the patient's body. In this system:

said probe (1) consists of a rod (2) comprising fastening means (3) to an electronic measuring unit (41, 42), the sensor of said parameter is included in the electronic measurement unit (41, 42) that also includes other parts consisting of electronic means associated with the sensor to provide a measurement signal, means for remote transmission of the measurement signal, power supply means for said parts, the measurement unit (41, 42) also comprising additional fastening means besides those of the rod (2) of the probe (1), the means for emitting an electric signal representing said parameter to the data processing device are receiver means positioned such that they are capable of receiving the measurement signal emitted by the remote transmission means.

25 Claims, 4 Drawing Sheets

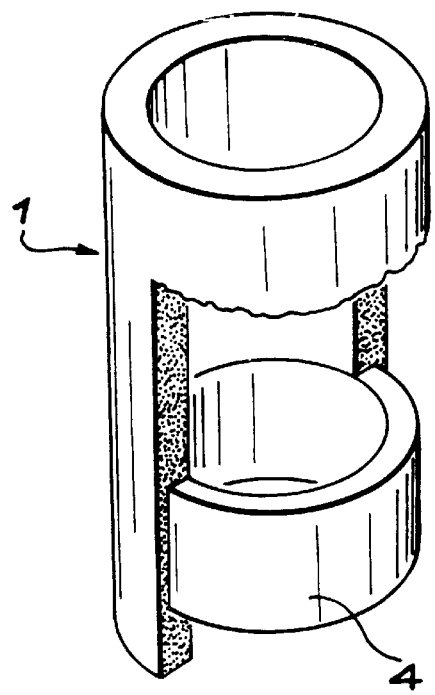
FIG. 2
FIG. 1
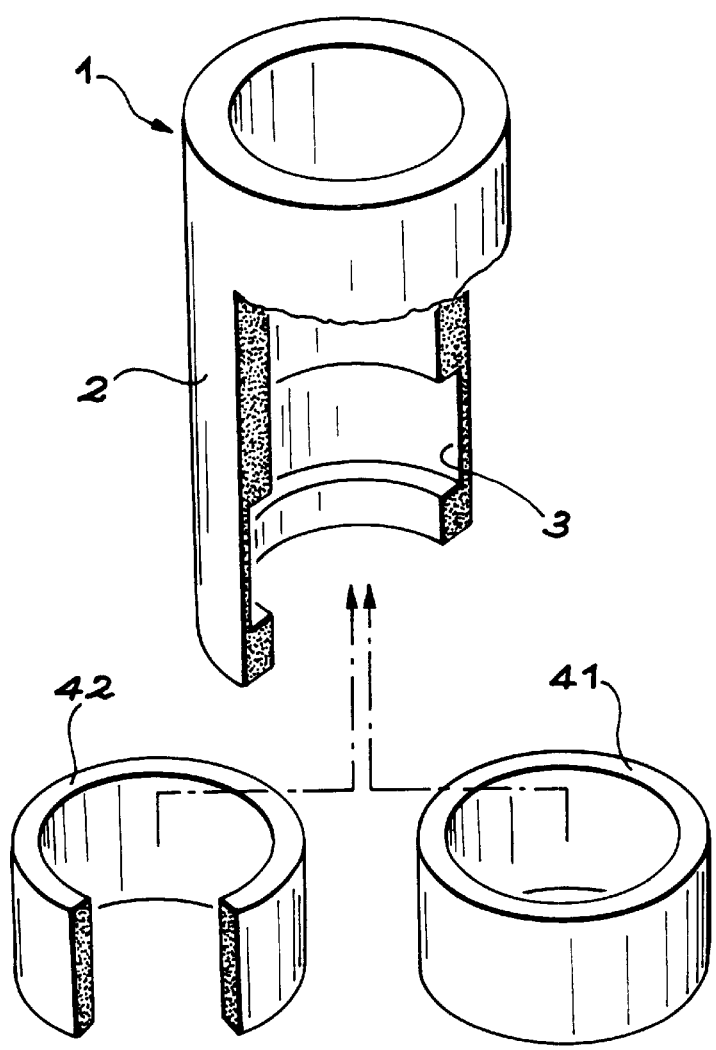

SYSTEM FOR MEASURING PHYSICAL PARAMETERS WITH A MEDICAL PROBE

This application is a national phase of PCT/FR99/01168 which was filed on May 17, 1999, and was not published in English.

FIELD OF THE INVENTION

The present invention relates to the measurement of one or more physical parameters using a medical probe.

STATE OF PRIOR ART

Medical probes or catheters are used to dispense a fluid inside the body of a patient and/or to measure certain physical parameters inside the body. The parameters may be parameters linked to dispensing fluid, such as the flow-rate or chemical composition, or simply environmental parameters such as pressure, temperature, humidity or pH. The fluid may be a liquid, for example, as when taking intravascular or urinary measurements, or gaseous as when taking pulmonary measurements.

For measuring distal pressure, i.e. at the end of the probe inside the body, the standard method consists in transferring the measurement to a proximal location, i.e. to the outside of the probe in order to measure the pressure with a standard electronic sensor that does not have to be miniaturised. Two main techniques can be used for the interface that enables the pressure to be transmitted: using a liquid mandrel or a gaseous mandrel. These techniques create problems, however, in terms of reliability, user friendliness and accuracy. The direct use of gas as an interface causes damping of the measured signal and is unreliable as the patient's secretions can block the pressure reading. The liquid-mandrel technique has the advantage of being based on the use of an incompressible interface. It can be used to measure liquids but also to measure gas pressures when a suitable interface is used, as described in U.S. Pat. No. 4,813,431. There is, however, a risk of air bubbles appearing in the column and is therefore potentially dangerous for the patient. In this event steps are required to remove the bubbles. Furthermore, the high density of water in the liquid column creates a difference between the pressure read and the internal pressure that is dependent on the variation in altitude between the two points. International patent 95/22,280 describes a method using laser measurements to estimate this difference but the technique requires a device that is expensive and far from practical to use.

Probes and catheters are used for different applications in the medical sector but on the whole the requirements and technical problems are identical. A particularly significant example is that of mechanical ventilation.

The mechanical ventilation of a patient in intensive care may continue over several weeks, even several months. Specialist s often use "pressurised" ventilation techniques in which the ventilator must reach a level of pressure (controlled pressure) or facilitate patients' inspiration (assisted pressure). The respirator is guided by the patient's reactions that it receives via flow-rate- or pressure-sensors. The aggressiveness of the ventilation techniques is preferably limited in order to prevent the patients' state of health from worsening, accelerate their recovery and gradually encourage patients to breath on their own again. When patients still have or have regained their breathing reflexes they trigger gas to be dispensed from the respirator. It is therefore essential for sensors, particularly pressure sensors, to be sensitive and reliable in order for mechanical ventilation to be suited to patients' actual requirements.

At present the pressure sensors are located on the external circuit that connects the patient to the mechanical respirator. The signals emitted by the sensors do not reflect the actual conditions in vivo due to the difference caused by the connecting parts, particularly the intubation probe. This phenomenon is particularly noticeable in the phase during which the probe is removed from the patient when the flow rates are immediately increased. The gaseous mandrel technique is marketed by all the probe producers but it is too unreliable for use in controlling the respirator directly.

Direct, reliable measurements of the pressure inside the respiratory tracts result in significant progress for the safety of patients and open the way to developing ventilation techniques with improved performance characteristics that will reduce the average stay in intensive care units and will therefore have a positive effect on hospital costs. The usefulness of such techniques is increased with the new, high frequency ventilation methods used on adults and particularly young children, for whom no accurate routine monitoring means are currently available.

Another example concerns urodynamics. Certain urology examinations require liquid to be injected into the patient's bladder and the changes in pressure to be monitored. At present catheters fitted with instruments that include electronic-pressure sensors, which are also very fragile, are expensive. They are therefore mainly reserved for research applications. Consequently, measuring the physiological liquid-supply pressure is preferred. The technique is, however, difficult to implement and unreliable due to the problems caused by removing bubbles and the pressure difference resulting from the height of the column of injected liquid.

Another example concerns the probes used in the cardiovascular sector. The arterial pressure is measured outside the body at the proximal end of a catheter filled with pressurised physiological liquid. This technique requires the use of a pocket of pressurised serum and a control valve that take up space around the patient unnecessarily. This application illustrates the use of a catheter containing a pressure sensor but that does not dispense a fluid.

A technique is therefore required, particularly for measuring pressure, that integrates the electronic sensor directly at the end of the probe or catheter in the actual place where the measurement is necessary. The requirement extends to measuring several parameters at the end of a catheter.

For reasons of hygiene the probes are preferably used once only. Ideally they should therefore be produced for a moderate cost price. They are produced using extrusion techniques that enable the cost objectives to be reached, even for medium-sized production runs. The techniques are restricting in terms of materials and shapes as they require the probe to be symmetrical around the longitudinal axis. Techniques are known that enable probes to be produced with an end in a different material from that of the probe body (see for example U.S. Pat. No. 3,890,976 and international patent 94/00174). Techniques are known for measuring pressure at the end of a probe using an electronic sensor that is implanted directly in the probe and that is connected to the outside of the patient's body by leads. They are used to measure intratracheal pressure (see international patent 94/22518) or arterial pressure (see international patent 97/17888). Multiplexing techniques have been described to enable a single pair of leads to be used (see U.S. Pat. No. 4,432,372). These techniques, however, lead to significant increase in cost that arises from the sensor being fastened inside the probe and the electrical connections that are not directly compatible with the extrusion techniques. Their use is therefore limited to only a few applications.

In general, and particularly concerning pressure, the production of microsensors is dependent on the microtechnology that is currently being developed through the progress made in the microelectronics industry. The techniques that are being developed today enable mechanical functions to be integrated into electronic components and miniature electronic sensors to be designed. Compared to standard mechanical sensors the new sensors are more sensitive, more reliable and multi-purpose because they are capable of being connected to a signal processing unit.

For pressure sensors in particular, various techniques for measuring the distortion of a membrane have been proposed for use in these systems. Piezoresistive techniques are used to measure the distortion of a piezoresistive part placed on the surface of a membrane. The pressure is determined by measuring variations in resistance. Today this technique is limited by the minimum size of the pressure sensor required and the consumption of the detection system. The use of an optical system (see U.S. Pat. No. 5,546,939) for measuring distortion simplifies the problems of electrical connections but it is difficult to use for measuring several parameters and does not enable in situ signal processing to be integrated. Capacitance techniques are currently the most promising in terms of space requirements and power consumption. They require, however, a capacitance variation electronic processing system to be available in the immediate vicinity.

Microsensors are usually connected to data processing devices by connecting wires or optical fibres. U.S. Pat. No. 4,127,110 describes a version of a wireless microsensor that is used with capacitance sensors to measure intracranial pressure. The capacitance of the sensor is used as the basis of an L-C circuit the resonance frequency of which measures the variations in pressure. This technique is, however, limited to obtaining a single parameter and the transmission of the measurement is necessarily analogue, which limits its accuracy. U.S. Pat. No. 4,556,063 proposes extending this technique to measuring several parameters in implanted circuits that have a battery power supply. This technique is currently used to programme heart pacemakers. Following the progress made in miniaturisation it is possible to apply remote power supply and remote transmission techniques using miniaturised circuits. These techniques have the advantage of providing greater flexibility in terms of processing. Their application to systems that only use passive measuring circuits is known for implantable systems (for example see U.S. Pat. No. 5,704,352).

The main problem when using microsystem-based components in medical probes is the cost of integrating them.

DISCLOSURE OF THE INVENTION

In order to provide a solution to the problem described above, it is proposed that the mechanical part of the probe (the rod) that is produced using a standard, inexpensive technique without incorporating any electronic components or electrical connectors, and then adding an electronic measurement unit that comprises one or more sensors, a local miniaturised electronic circuit that enables the measurement signal to be processed and a component that transmits the measured values and receives a remote power supply signal.

The aim of the invention is therefore to provide a system for measuring at least one physical parameter in a place in a patient's body to which a medical probe has access, comprising a medical probe equipped with a sensor of the said parameter and means to emit an electronic signal representing the said parameter that is received by the sensor, to a data processing device outside the patient's body, characterised in that:

said probe consists of a rod comprising means to fasten it to an electronic measuring unit, the sensor of said parameter is included in the electronic measurement unit that also includes other parts consisting of electronic means associated with the sensor to provide a measurement signal, means for remote transmission of the measurement signal, power supply means for the electric means associated with the sensor and remote transmission means, the measurement unit also comprising additional fastening means besides those of the rod of the probe, the means for emitting an electronic signal representing said parameter to the data processing device are receiver means positioned such that they are capable of receiving the measurement signal emitted by the remote transmission means, the remote transmission means comprise a coil-shaped antenna, the power supply means comprise a circuit capable of being charged by a remote power supply using said coil.

The fastening means of the rod may comprise a housing that enables the measurement unit to be inserted. If the rod is hollow said housing may be provided in the internal wall of the rod. The measurement unit may be ring shaped, said housing constituting an annular throat in the rod. If the measurement unit is a closed ring the rod may be produced in a material that is sufficiently elastic to enable the measurement unit to be inserted into the housing due to distortion of the rod. The rod can also comprise a narrowing against which the measurement unit comes to stop. In this event the rod can also comprise an anchoring system that retains the measurement unit in the housing. The measurement unit can be an open ring that clips into place in said housing.

The fastening means between the measurement unit and the rod may comprise contact surfaces between the measurement unit and the rod. The fastening means between the measurement unit and the rod may comprise an adhesive substance or be based on moulding techniques.

The receiver means may be positioned on the end of the probe that is outside the patient's body. They can also be means that may be placed on the patient's body.

The remote transmission and reception means can be radio-frequency, infrared or ultrasound communication means.

Advantageously, the measurement unit comprises a connection plane provided with conductor paths that ensure electrical connection between the various components of the measurement unit. The connection plane may consist of a flexible substrate that is coiled into a tube shape and imbedded in a moulding substance. The components of the measurement unit can have electrical contacts welded onto certain conductor paths selected from said conductor paths. They can be components inserted into the measurement unit, said insertion creating electrical contact between these components and the conductor paths selected from among said conductor paths.

As the remote transmission and reception means are radio-frequency communication means, the measurement unit can comprise an antenna produced by metallisation being deposited on the flexible substrate. The antenna can be an added part that is connected to the connection plane and imbedded in the moulding substance. It can also be positioned around the measurement unit.

For mechanical ventilation purposes the medical probe can be an intubation probe capable of dispensing gas. It can also be a urinary probe capable of taking urodynamic measurements or a catheter capable of taking intravascular pressure.

BRIEF DESCRIPTION OF THE DRAWINGS

Other characteristics, aims and advantages of the present invention will be better understood from the following detailed description. The description is of a non-limitative example and refers to the attached figures where:

FIG. 1 shows how a medical probe of the measurement system of the present invention can receive the electronic measurement unit with which it is associated;

FIG. 2 shows a medical probe of the measurement system of the present invention equipped with an electronic measurement unit;

DETAILED DESCRIPTION OF EMBODIMENTS OF THE INVENTION

The measurement system of the present invention offers the advantage of using a medical probe that is easy to produce and inexpensive. It is produced advantageously by extrusion using techniques well known to those skilled in the art.

As shown in FIG. 1, probe 1 can consist of a tube 2 provided with a housing near one of its ends into which an electronic measurement unit can be inserted. In the example shown housing 3 constitutes a ring-shaped housing in the inner wall of tube 2. Housing 3 is capable of receiving a measurement unit shaped to suit the housing. In order to maintain fluid communication between the two ends of the probe the measurement unit can be advantageously ring shaped.

Figure 2A:
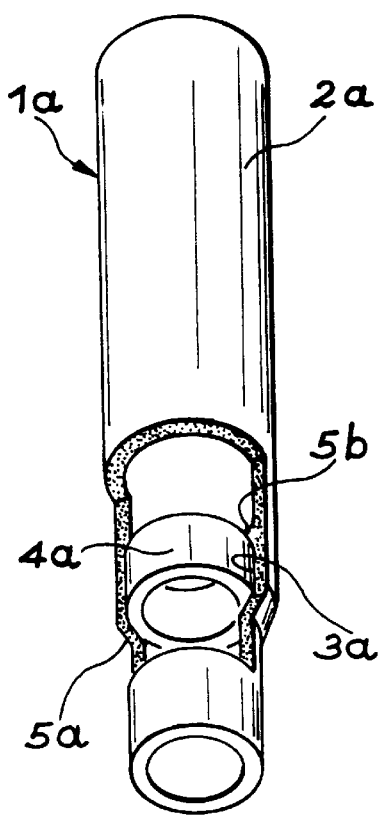
FIGS. 2A and 3 show other methods of combining a medical probe and an electronic measurement unit for a measurement system of the present invention.

FIG. 2 shows a medical probe 1 equipped with a measurement unit 4. As shown in FIG. 1 the measurement unit can either be a closed ring 41 or an open ring 42. If the measurement unit is a closed ring rod 1 is designed such that the wall is capable of distorting elastically in order to receive the unit. If the measurement unit is an open ring, it can be inserted into its housing and pressure applied to its diameter to reduce said diameter in the manner of a clip system. Another method of inserting the measurement unit in the rod of the probe is shown in FIG. 2A. Tube 2a of probe 1a includes a narrowing 5a at the distal end. Measurement unit 4a, with internal and external diameters that are identical to those of the narrowing, is inserted into tube 2a via the proximal end. It is pushed until it comes to stop against narrowing 5a. An anchoring system 5b holds the unit in place in housing 3a to prevent it from working back up the tube.

In these embodiments the instruments can be fitted to the probe under sterile conditions before the probe is used, the physician selecting the unit suited to the requirements of the examination to be performed.

Figure 3:
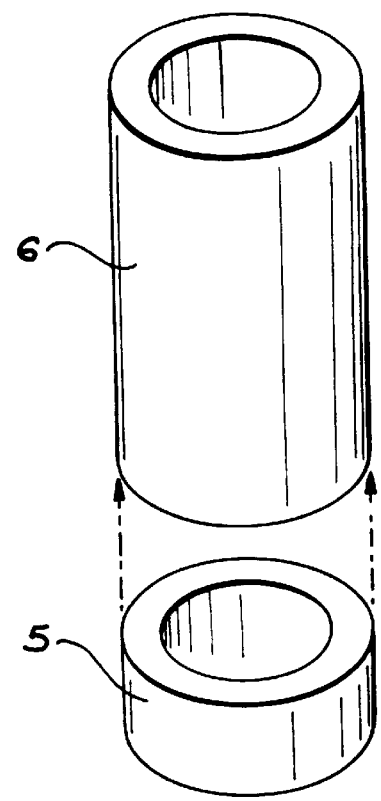

FIG. 3 shows another method of fastening a measurement unit to the rod of a medical probe. In this version tubular-shaped measurement unit 5 is fastened to the end of rod 6 that constitutes the probe and that is also tubular-shaped. The unit can be fastened to the tube using an adhesive substance or a moulding technique. Parts 5 and 6 can simply be put end to end. Measurement unit 5 can also partly or totally penetrate tube 6. Fastening can then be performed during a production stage of the measurement system.

The measurement unit can comprise several sensors to measure as many physical parameters and electrical components associated with the sensors as well as electrical connections between the various parts. The unit can also comprise a transmitter antenna if measurements are to be transmitted by radio frequency. Measurements are transmitted using a receiving antenna. The receiving antenna may be located outside the patient's body, transmission then being effected through the patient's skin. The receiver can be fastened to the patient's skin like an electrocardiograph electrode. The receiving antenna can also be located inside the wall of the probe or inside the probe. The receiver is connected by leads to a device that processes data supplied by the sensors, whether the receiver is fastened to the patient's skin outside the patient's body or is inside the patient inside the probe. The connection may be achieved via a signal analysis device or a direct connection may be made to the monitoring machine. The receptor, analysis device or monitoring machine may comprise reference sensors, particularly for pressure.

Figure 4:
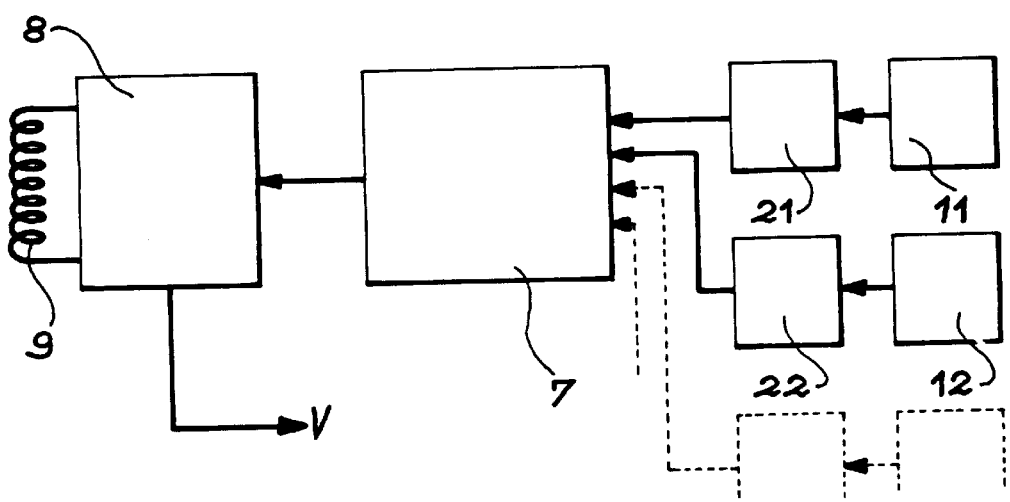
FIG. 4 is a functional drawing of the electronic measurement unit of the measurement system of the present invention.

FIG. 4 is a possible functional drawing for the electronic part of the measurement sensor. Each sensor 11, 12, etc. is associated with a digital converter circuit 21, 22, etc. respectively, the outputs of which are connected to the inputs of a signal processing circuit 7. Various physical parameters can therefore be measured: pressure, temperature, chemical composition, pH and the moisture content of a gas. Signal processing circuit 7 emits a signal representing the various measurements that have been taken to a transmitter circuit 8. The measurements can be transmitted separately or as a combined multi-parameter variable. Antenna 9 is used to perform the transmission.

A battery can be incorporated into the measurement unit to ensure the power supply to the electronic components of the unit. Remote transmission can also be used to ensure the power supply. If antenna 9 is coil shaped it is possible to use induction to supply the measurement unit with power. In this situation a circuit converting the AC voltage to DC voltage V can be added to transmitter circuit 8.

A self-calibrating system can be integrated into the measurement unit to compensate for the differences introduced in the conversion system. A unit confirmation signal can also be included in the transmission of measurement signals.

Figure 5:
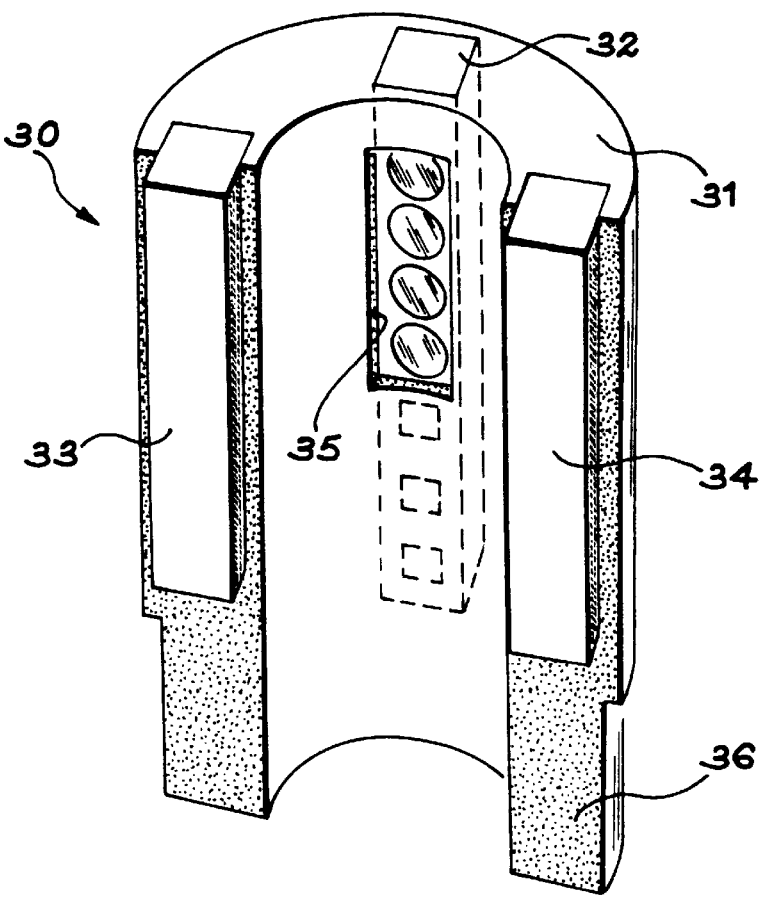
FIG. 5 is a cross section of an electronic measurement unit for a measurement system of the present invention.

FIG. 5 is a longitudinal cross-section of measurement unit 30 of the present invention. Annular body 31 is used as a mechanical substrate for all the electronic components that constitute the electronics. Said annular body is moulded. Housings are provided within the annular body 31 itself to contain a component 32 that contains in itself the various sensors and components 33 and 34 that contain the other circuits. The various components and conductor paths for the electrical connections are divided over a connection plane. Sensors that do not need to be in direct contact with the environment to be characterised, for example a temperature sensor, are imbedded in annular body 31. A window 35 is provided in annular body 31 for the other sensors. The surface is nevertheless protected to avoid problems of humidity affecting the electrical contacts and from the effect of a possible deposit on the sensitive surface of the sensors that are not imbedded.

In order to measure pressure the sensors are preferably absolute pressure microsensors that are capacitive and optimised to operate within the 700–1400 mbar range. They are provided with one or two contacts that give access to a measurement capacitance and possibly a reference capacitance. A dedicated electronic processing circuit is associated with each type of sensor depending on the electrical-parameter type associated with each sensor, i.e. a resistance, capacitance or inductance measurement. The processing comprises at least one digital conversion of the measured signal.

The capacitance sensors are associated with ASIC (Application Specific Integrated Circuit) circuits that enable a variable capacitance to be compared with a reference capacitance. The difference between the two capacitances is transformed directly into a digital signal for example using a system based on the principle of switched capacitors. The same principle can be applied to resistance measurements.

Measurement unit 30 comprises a section 36 with a reduced external diameter that enables the antenna coil to be wound around it if necessary.

Figure 6:
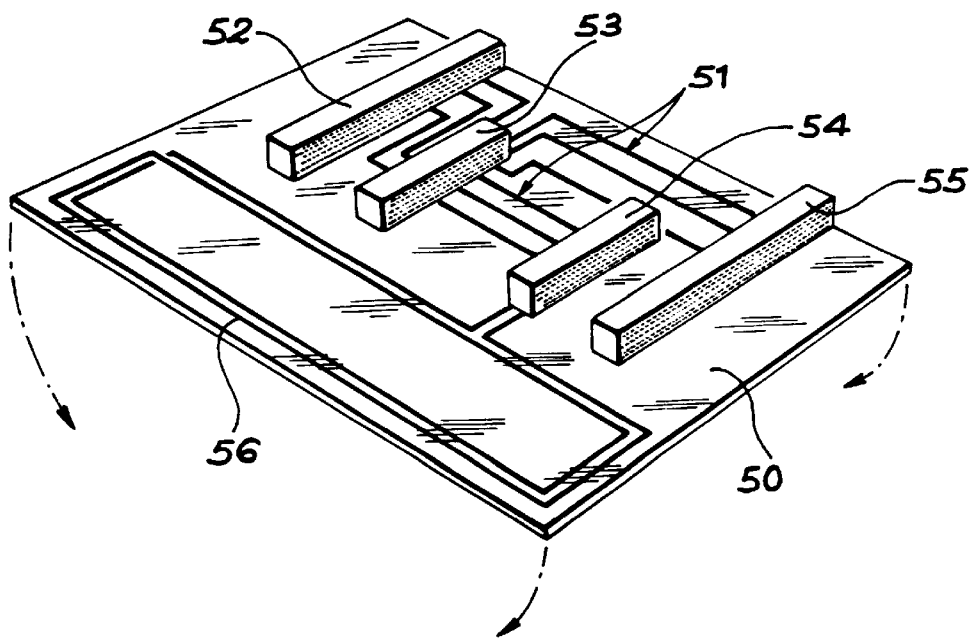
FIG. 6 shows the method used to produce an electronic measurement unit for a measurement system of the present invention.

FIG. 6 shows a stage in the production of a measurement unit for a measurement system of the invention. The connection plane consists of a Kapton-type flexible substrate 50, one of the surfaces of which has conductor paths 51 that provide electrical connections between the electronic components of the unit. The conductor paths can be produced by metallization, screen printing or copper electro-plating. The electronic components, for example components 52, 53, 54 and 55 are fastened to flexible substrate 50. A window is provided in the flexible substrate for the sensors that need to be in contact with the fluid whose physical parameters are to be measured.

Antenna 56 can also be deposited on flexible substrate 50 using the same techniques as for the conductor paths.

In a first stage, components 52 to 55 are positioned on flexible substrate 50, the surfaces of the components that comprise the electrical contacts and the sensitive zones of the sensors being turned towards the flexible substrate. The fusible micropellets that are deposited on each electrical contact when they are produced or on the contacts of the flexible substrate, are slightly heated so that they melt.

In a second stage the flexible substrate is curved, as shown by the arrows in FIG. 6, and is positioned inside a mould in order to obtain the unit body. This operation provides the unit with the required rigidity.

The mechanical and electrical connections can also be made after the substrate has been shaped.

Figure 7:
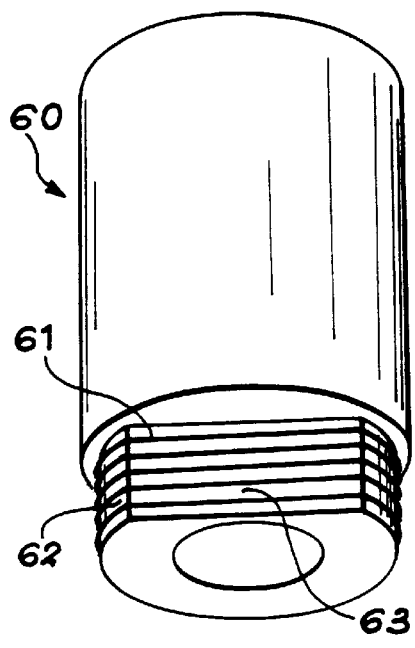
FIGS. 7 and 8 show two versions of electronic measurement units for a measurement system of the present invention, equipped with external antennas.
Figure 8:
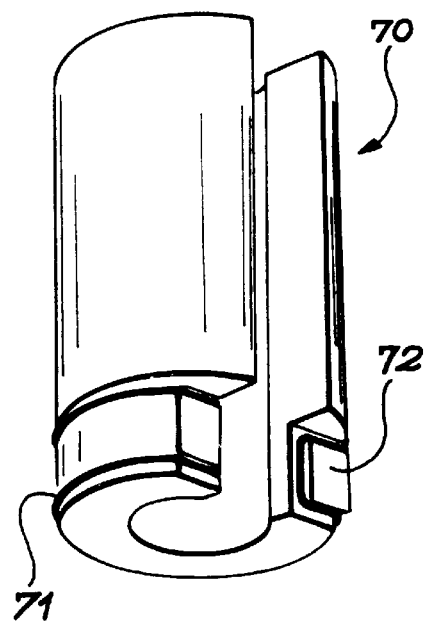
Figure 9:
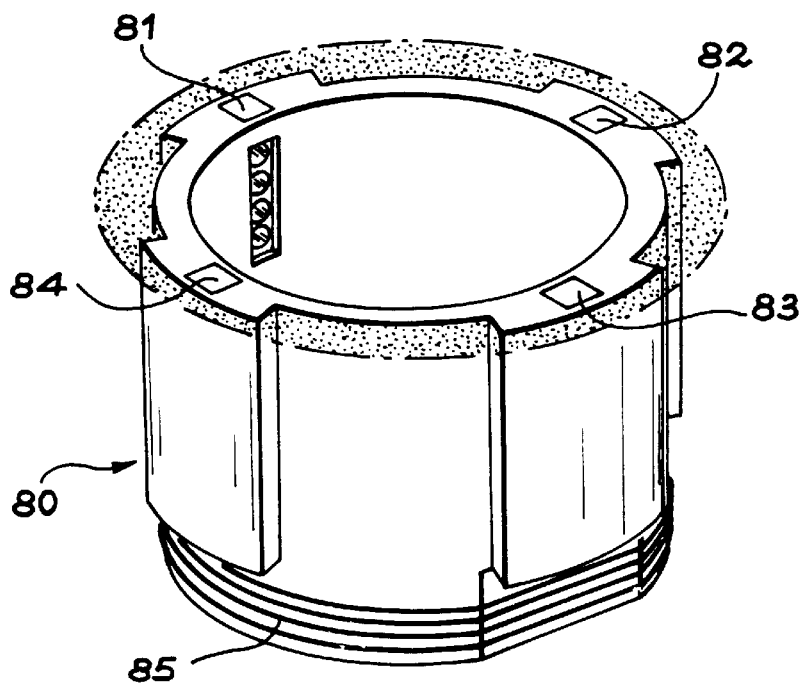
FIG. 9 shows an electronic measurement unit for a measurement system of the present invention, this unit being designed for a medical probe with a thin wall.

The transmitter antenna can be inserted during the moulding operation if it is not included directly on the flexible substrate. The transmitter antenna can also be wound around the body of the measurement unit, as shown in FIGS. 7, 8 and 9. In any event, the shape of the unit body is such that the antenna is connected to the rest of the unit electronic circuit in the connection plane.

In another embodiment the electronic components are pre-assembled or integrated within a single circuit. This single circuit is then integrated in the unit body and connected to the antenna using the techniques described above.

FIG. 7 shows a tubular-shaped measurement unit 60 the antenna 61 of which is wound around the outside of the unit body. Antenna 61 is wound around a section 62 of the measurement unit body the diameter of which is smaller than the rest. A flat section 63 is provided on section 62 to enable the antenna to be connected directly to the connection plane.

FIG. 8 shows a measurement unit 70 that has a clip-type longitudinal opening, antenna 71 of which is wound around a protruding section 72. The axis of the antenna can be either parallel or perpendicular to the axis of the probe.

If the probe has a thin wall and if an annular measurement unit is to be inserted into the probe, the unit is preferably shaped like that shown in FIG. 9. The measurement unit 80 shown in this figure has areas of different thickness. The thickness of the areas containing electrical components 81, 82, 83 and 84 is suited to the integration of said components. The areas between the regions containing components are thinner. The thickness of the probe corresponding to this measurement unit is shown by the shaded areas. The thin areas of the measurement unit match the thick areas of the probe. This method avoids weakening the probe throughout its entire thickness. FIG. 9 shows the antenna 85 wound around unit 80.

The measurement unit of the measurement system according to the present invention can also be a part moulded in several sections containing housings for the sensors and the other electronic components.

The sensors that are not imbedded in the measurement unit body and the transmitter antenna (if visible) can be protected by a gel being deposited and/or a thin film of polymerised biocompatible elastomer being fastened in situ or by thermowelding.

What is claimed is:

1. System for measuring at least one physical parameter in a place in a patient's body to which a medical probe has access, comprising a medical probe equipped with a sensor of said parameter and means for emitting an electrical signal that represents said parameter and that is received by the sensor, to a data processing device outside the patient's body, wherein:

said probe consists of a rod comprising fastening means to fasten an electronic measuring unit to the rod, the sensor of said parameter is included in the electronic measurement unit that also includes other parts consisting of electronic means associated with the sensor to provide a measurement signal, means for remote transmission of the measurement signal, power supply means of the electric means associated with the sensor and remote transmission means, wherein:

the measurement unit also comprises additional fastening means besides those of the rod of the probe, the means for emitting an electronic signal representing said parameter to the data processing device are receiver means positioned such that they are capable of receiving the measurement signal emitted by the remote transmission means, the remote transmission means comprise a coil-shaped antenna, the power supply means comprise a circuit capable of being charged by a remote power supply using said coil, the sensor is located at the distal end of the medical probe.

2. Measurement system of claim 1 wherein the fastening means of the rod comprise a housing that enables the measurement unit to be inserted.

3. Measurement system of claim 2 wherein said rod is hollow, said housing is provided in the internal wall of the rod.

4. Measurement system of claim 3 wherein the measurement unit is ring shaped, said housing constituting an annular throat in the rod.

5. Measurement system of claim 4 wherein said measurement unit is a closed ring, the rod is produced in a material that is sufficiently elastic to enable the measurement unit to be inserted into the housing due to distortion of the rod.

6. Measurement system of claim 4 wherein the measurement unit is an open ring that clips into place in said housing.

7. Measurement system of claim 3 wherein the rod comprises a narrowing against which the measurement unit comes to stop.

8. Measurement system of claim 7 wherein the rod comprises an anchoring system that retains the measurement unit in the housing.

9. Measurement system of claim 1 wherein the fastening means between the measurement unit and the rod comprise contact surfaces between the measurement unit and the rod.

10. Measurement system of claim 9 wherein the fastening means between the measurement unit and the rod comprise an adhesive substance.

11. Measurement system of claim 1 wherein the receiver means are positioned on the proximal end of the probe.

12. Measurement system of claim 1 wherein the receiver means are means that may be placed on the patient's body.

13. Measurement system of claim 1 wherein the remote transmission means and reception means are radio-frequency communication means.

14. Measurement system of claim 1 wherein the remote transmission means and reception means are infrared communication means.

15. Measurement system of claim 1 wherein the remote transmission means and reception means are ultrasound communication means.

16. Measurement system of claim 1 wherein the measurement unit comprises a connection plane provided with conductor paths that ensure electrical connection between the various components of the measurement unit.

17. Measurement system of claim 16 wherein the connection plane consists of a flexible substrate that is coiled into a tube shape and that is imbedded in a moulding substance.

18. Measurement system of claim 17 wherein the components of the measurement unit have electrical contacts welded onto certain conductor paths selected from said conductor paths.

19. Measurement system of claim 17 wherein as the remote transmission and reception means are radio-frequency communication means, the measurement unit comprises an antenna produced by metallisation being deposited on the flexible support.

20. Measurement system of claim 16 wherein the components of the measurement unit are components inserted into the measurement unit, said insertion creating electrical contact between said components and the conductor paths selected from among said conductor paths.

21. Measurement system of claim 16 wherein said remote transmission and reception means are radio-frequency communication means, the measurement unit comprises an antenna that is an added part connected to the connection plane and imbedded in the moulding substance.

22. Measurement system of claim 16 wherein said remote transmission and reception means are radio-frequency communication means the measurement unit comprises said antenna wound around the measurement unit.

23. Measurement system of claim 1 characterised in that said probe is an intubation probe capable of dispensing gas for mechanical ventilation purposes.

24. Measurement system of claim 1 wherein said probe is a urinary probe capable of taking urodynamic measurements.

25. Measurement system of claim 1 wherein said probe is a catheter capable of measuring blood pressure.

* * * * *